United States Patent
Jaffe et al.

(10) Patent No.: US 10,376,463 B2
(45) Date of Patent: Aug. 13, 2019

(54) OCULAR IONTOPHORETIC DELIVERY OF DEXAMETHASONE AND FORMULATIONS THEREOF

(75) Inventors: Mike Jaffe, East Hartford, CT (US); Gary Cook, Westford, MA (US); Perry Calias, Melrose, MA (US); Michael A. Patane, Andover, MA (US)

(73) Assignee: Eyegate Pharmaceuticals, Inc., Waltham, MA (US)

( * ) Notice: Subject to any disclaimer, the term of this patent is extended or adjusted under 35 U.S.C. 154(b) by 353 days.

(21) Appl. No.: 13/469,481

(22) Filed: May 11, 2012

(65) Prior Publication Data
US 2012/0283231 A1   Nov. 8, 2012

Related U.S. Application Data

(62) Division of application No. 12/391,836, filed on Feb. 24, 2009, now abandoned.

(60) Provisional application No. 61/031,267, filed on Feb. 25, 2008, provisional application No. 61/047,950, filed on Apr. 25, 2008.

(51) Int. Cl.
| A61K 9/00 | (2006.01) |
| A61N 1/04 | (2006.01) |
| A61F 9/00 | (2006.01) |
| A61K 31/573 | (2006.01) |
| A61K 41/00 | (2006.01) |
| A61N 1/30 | (2006.01) |

(52) U.S. Cl.
CPC .......... *A61K 9/0048* (2013.01); *A61F 9/0008* (2013.01); *A61K 9/0009* (2013.01); *A61K 31/573* (2013.01); *A61K 41/00* (2013.01); *A61N 1/0448* (2013.01); *A61N 1/303* (2013.01); *A61N 1/044* (2013.01)

(58) Field of Classification Search
None
See application file for complete search history.

(56) References Cited

U.S. PATENT DOCUMENTS

| 4,221,787 A | 9/1980 | Bodor et al. |
| 4,279,900 A | 7/1981 | Bodor et al. |
| 4,443,440 A | 4/1984 | Anderson et al. |
| 4,456,602 A | 6/1984 | Anderson et al. |
| 4,469,689 A | 9/1984 | Anderson et al. |

(Continued)

FOREIGN PATENT DOCUMENTS

| CN | 1164392 A | 11/1997 |
| EP | 1080731 A2 | 3/2001 |

(Continued)

OTHER PUBLICATIONS

Shah et al. Thermodynamic characterization of dexamethasone sodium phosphate and its complex with DNA as studied by conductometric and spectroscopic techniques. J. Clin. Chem. Soc., 54, No. 2, 2009.*

(Continued)

*Primary Examiner* — Marcos L Sznaidman
*Assistant Examiner* — Rayna Rodriguez
(74) *Attorney, Agent, or Firm* — McCarter & English, LLP; Steven G. Davis; Michael J. DeGrazia

(57) ABSTRACT

Disclosed herein are formulations of dexamethasone or a prodrug thereof suitable for delivery by ocular iontophoresis and methods of use thereof.

1 Claim, 10 Drawing Sheets

(56) References Cited

U.S. PATENT DOCUMENTS

| | | | |
|---|---|---|---|
| 4,472,392 | A | 9/1984 | Anderson et al. |
| 4,588,718 | A | 5/1986 | Anderson et al. |
| 5,222,936 | A | 6/1993 | Stephen et al. |
| 5,525,492 | A | 6/1996 | Hill |
| 5,621,002 | A | 4/1997 | Bosslet et al. |
| 5,945,404 | A | 8/1999 | Sugai et al. |
| 5,955,100 | A | 9/1999 | Bosslet et al. |
| 6,028,066 | A | 2/2000 | Unger et al. |
| 6,090,800 | A | 7/2000 | Unger et al. |
| 6,154,671 | A | 11/2000 | Parel et al. |
| 6,395,756 | B2 * | 5/2002 | Trimming et al. ............ 514/324 |
| 6,650,934 | B2 | 11/2003 | Murdock |
| 7,164,943 | B2 | 1/2007 | Roy |
| 8,030,297 | B2 | 10/2011 | Lichter et al. |
| 8,048,448 | B2 | 11/2011 | Ludwig et al. |
| 2002/0099357 | A1 | 7/2002 | Parkinson et al. |
| 2003/0023228 | A1 * | 1/2003 | Parkinson et al. ............ 604/521 |
| 2005/0245497 | A1 * | 11/2005 | Penfold et al. ................ 514/179 |
| 2005/0245856 | A1 | 11/2005 | Roy |
| 2006/0110428 | A1 | 5/2006 | deJuan et al. |
| 2006/0142706 | A1 | 6/2006 | Roy et al. |
| 2007/0060859 | A1 * | 3/2007 | Kanamura et al. ............. 604/20 |
| 2007/0123814 | A1 | 5/2007 | Roy |
| 2007/0219170 | A1 | 9/2007 | Samson et al. |
| 2008/0027371 | A1 | 1/2008 | Higuchi et al. |
| 2008/0119448 | A1 * | 5/2008 | Friedlaender ................. 514/179 |
| 2009/0326438 | A1 * | 12/2009 | Karashima ...................... 604/20 |

FOREIGN PATENT DOCUMENTS

| | | | |
|---|---|---|---|
| EP | 1177814 | A1 | 2/2002 |
| JP | 2006-518769 | * | 8/2006 |
| WO | 200122936 | A1 | 4/2001 |
| WO | 2002058789 | A1 | 8/2002 |
| WO | 2004087043 | A2 | 10/2004 |
| WO | 2005021008 | A1 | 3/2005 |
| WO | 2006/072887 | | 7/2006 |

OTHER PUBLICATIONS

Translation JP 2006-518769. 2014.*
4Zimuth et al.; "Acid dissociation constant"; Wikipedia [http://en.wikipedia.org/w/index.php?oldid=519426120—Downloaded: Nov. 6, 2012].
Lam et al.; "A histopathologic study of retinal lesions inflicted by transscleral iontophoresis"; Graefe's Arch. Clin. Exp. Ophthalmol.; 1991; pp. 389-394; vol. 229; Springer-Verlag; U.S.
Anderson et al.; "Effects of Iontophoresis Current Magnitude and Duration on Dexamethasone Depostition and Localized Drug Retention"; Physical Therapy; 83(2):161-170 (2003).
Bourlais et al.; "Ophthalmic drug delivery systems—Recent advances"; Prog. Retin Eye Res.; 17:33-58 (1998).
Cohen et al.; "Evaluation of Dexamethasone Phosphate Delivered by Ocular Lontophoresis for Treating Noninfectious Anterior Uveitis"; Ophthalmology; xx:xxx Published Online, Nov. 23, 2011).
Ding; "Recent Developments in Ophthalmic Drug Delivery"; Pharm. Sci. Tech. Today; 1:328-335 (1998).
Dorwald; Side Reactions in Organic Synthesis: A Guide to Successful Synthesis design; Weinheim; Wiley-VCH; Verlag GmbH & Co KGaA (2005) [Preface].
Eljarrat-Binstock et al.; "Transcorneal and transscleral iontophoresis of dexamethasone phosphate using drug loaded hydroget"; J. Controlled Release; 106:386-390 (2005).
Eljarrat-Binstock et al.; "Iontophoresis: A Non-invasive Ocular Drug Delivery"; Journal of Controlled Release; 110:479-489 (2006).
Flynn et al.; "Factors Influencing Solvolysis of Corticosteroid 21-Phosphate Esters"; J. Phar. Sci.; 59:1433-1438 (1970).
Garrett et al.; "The Solvolysis of 21-Hydrocortisone Esters and Hemiesters"; J. Med. Pharm. Chem.; 5:112-133 (1962).
Hong et al.; "Recurrence after Topical Nonpreserved Methylprednisolone Therapy for Keratoconjunctivitis Sicca in Sjogren's Syndrom"; Ocul. Pharmacol. Ther.; 23:78-82 (2007).
Kawamura et al.; "Pharmaceutical Studies on Water-soluble Corticosteroid Derivatives II. Stability of Hydrocortisone 21-Aminoalkylcarboxylates in Solution"; Yakugaku Zasshi; 91(8): 863-870 (1971).
Kawamura et al.; "Pharmaceutical Studies on Water-soluble Corticosteroid Derivatives III. Stability of Hydrocortisone 21-Sulfobenzoates in Solution"; Yakugaku Zasshi; 91(8): 871-878 (1971).
Lallemand et al.; "A water-soluble prodrug of cyclosporine A for ocular application: A stability study"; Eur. J. Pharm. Biopharm.; 56:307-318 (2003).
Lam et al.; Transscleral Iontophoresis of Dexamethasone; Arch Ophthalmol; 107:1368-1371 (1989).
Marsh et al.; "Topical Nonpreserved Methylprednisolone Therapy for Keratoconjunctivitis Sicca in Sjogren Syndrome"; Ophthalmology; 106:811-816 (1999).
Mcghee et al.; "Locally Administered Ocular Corticosteroids: Benefits and Risks"; Drug Saf.; 25:33-55 (2002).
Patane et al.; "Ocular Iontophoresis of EGP-437 (dexamethasone phosphate) in dry eye patients: results of a randomized clinical trial"; Clin. Ophthal.; 5:633-643 (2011).
PCT International Search Report—(PCT/US2009/034977); dated Jun. 16, 2009.
Scoggin; "Prodrugs and Outpatient Medical Practice"; Bull. N.Y. Acad. Med.; 59(5):450-456 (1983).
Stella et al., Prodrugs: Challenges and Rewards—Part 1 (2007).
Yamamoto et al.; Pharmaceutical Studies on Water-soluble Corticosteroid Derivatives I. Stability of Hydrocortisone 21-Hemiesters in Solution; Yakugaku Zasshi; 91(8):855-862 (1971).
Hastings et al.; "VisulexTM: Advancing Iontophoresis for Effective Noninvasive Back-of-the-Eye Therapeutics"; Drug Delivery Technology; 4(3):1-10 [Retrieved from Internet][Posted: Mar. 28, 2008].
English Translation of Notice of Reasons for Rejection for related JP Application No. 2010-547849, 5 pp, dated Jul. 2013.
Parkinson, et al., "Tolerance of Ocular Iontophoresis Healthy Volunteers," Journal of Ocular Pharmacology and Therapeutics, vol. 19, No. 2, 2003, pp. 145-151
Behar-Cohen, et al., "Iontophoresis of Dexamethasone in the Treatment of Endotoxic-Induced-Uveitis in Rats," Experimental Eye Research, vol. 65, No. 65, Jan. 1, 1997, pp. 533-545.
Komaromy, et al., "Dexamethasone Application to the Canine Eye with Transscleral Coulomb-Controlled Iontophoresis (CCI)", IOVS, Annual Meeting of the Association-For-Research-In-Vision-and-Ophthalmology, vol. 46, No. Suppl. S, 2005, p. 477 (XP002733181).
Behar-Cohen, et al., "Transscleral Coulomb-Controlled Iontophoresis of Methylprednisolone into the Rabbit Eye: Influence of Duration of Treatment, Current Intensity and Drug Concentration on Ocular Tissue and Fluid Levels", Experimental Eye Research, vol. 74, No. 1, Jan. 1, 2002, pp. 51-59 (XP002733186).

* cited by examiner

OCULAR IONTOPHORETIC DELIVERY OF DEXAMETHASONE AND FORMULATIONS THEREOF

RELATED APPLICATIONS

This application is a divisional of U.S. application Ser. No. 12/391,836, filed Feb. 24, 2009, which claims priority to U.S. Provisional Application 61/031,267, filed Feb. 25, 2008, and U.S. Provisional Application 61/047,950, filed Apr. 25, 2008, the entire contents of each of which are incorporated herein by reference.

BACKGROUND

Corticosteroids are widely prescribed therapeutics. Systemic, topical and injected formulations are routinely employed for a variety of ophthalmic conditions. In particular, topical applications account for the widest use of non-invasively delivered corticosteroids for ocular disorders. This approach, however, suffers from low bioavailability and, thus, limited efficacy.

Dexamethasone, member of the glucocorticoid class of steroid hormones, acts as an anti-inflammatory and immunosuppressant. Ocular formulations are used that allow for diffusion of dexamethasone across an ocular membrane, however, such topical formulations suffer from slow, inadequate and uneven uptake. Because current ocular delivery methods achieve low ocular exposures, frequent applications are required and compliance issues are significant.

Topical dexamethasone applications involving ocular iontophoresis have not been described. Based on commercially-available, columbic-controlled iontophoresis for topical applications to the skin of a variety of therapeutics, it is clear that even well understood pharmaceuticals require customized formulations for iontophoresis. These alterations maximize dosing effectiveness, improve the safety and manage commercial challenges. The known technical formulation challenges presented by dermatological applications may translate in to ocular delivery. However, ocular iontophoresis presents additional formulation needs. Thus, developing novel formulations that are ideally suited for ocular iontophoretic delivery of corticosteroids is required. Such formulations include many variables, including: API concentration, solute, excipients, stabilizers, buffering agents, delivery applicator, iontophoretic dose, etc. Developing corticosteroids suitable for non-invasive local ocular delivery will significantly expand treatment options for ophthalmologists.

SUMMARY

Described herein are devices and methods for enhancing the delivery of negatively charged compounds into and through tissues, e.g., the eye. More specifically, the methods and devices described herein utilize iontophoresis to actively deliver a compound, e.g., dexamethasone phosphate, into a mammalian eye. The methods and devices focus on developing corticosteroid formulations and use of these formulations to maximize drag delivery, e.g., through iontophoresis, and patient safety. These novel formulations are suitable for treating a variety of inflammatory-mediated ocular disorders. The formulations, which include different strengths of the active pharmaceutical ingredient (API), are capable of being used with different iontophoretic doses (e.g., current levels and application times). These solutions can, for example: (1) be appropriately buffered to manage initial and terminal pHs, (2) be stabilized to manage shelf-life (chemical stability), and/or (3) include other excipients that modulate osmolarity. Furthermore, the drug product solutions are crafted to minimize the presence of competing ions. These unique dosage forms can address a variety of therapeutic needs. Ocular iontophoresis is a novel, non-invasive, out-patient approach for delivering substantial amounts of APIs into many ocular tissues. This non-invasive approach can lead to results comparable to or better than those achieve with ocular injections, without the significant risk of infection associated with the latter.

One embodiment is directed to a method for iontophoretically delivering a corticosteroid, corticosteroid derivative, prodrug or salt thereof into the eye of a subject, comprising: a) administering the compound to the eye of the subject; and b) performing ocular iontophoresis under conditions such that the pH is between about 2.5 and about 6.5, thereby delivering the compound into the eye. In a particular embodiment, the corticosteroid is a dexamethasone compound, derivative thereof. In a particular embodiment, the starting pH is about 5.7. In a particular embodiment, the corticosteroid is in the form of a prodrug. In a particular embodiment, the corticosteroid is delivered by injection prior to iontophoresis. In a particular embodiment, the method of injection is selected from the group consisting of: an intracameral injection, an intracorneal injection, a subconjonctival injection, a subtenon injection, a subretinal injection, an intravitreal injection and an injection into the anterior chamber. In a particular embodiment, the corticosteroid is administered topically prior to iontophoresis. In a particular embodiment, the topical administration comprises providing the corticosteroid in a form selected from the group consisting of: a liquid solution, a paste and a hydrogel. In a particular embodiment, the corticosteroid is embedded in a foam matrix. In a particular embodiment, the corticosteroid is supported in a reservoir. In a particular embodiment, the step of ocular iontophoresis is carried out prior to, during or after the step of administering the corticosteroid. In a particular embodiment, the compound is delivered by an iontophoretic dose of about $1.7 \times 10^{-4}$ mA·min to about 120 mA·min, e.g., between about 10 mA·min and about 30 mA·min. In a particular embodiment, the iontophoretic dose is about 20 mA·min. In a particular embodiment, the compound is delivered at a current of about 4.0 mA for a period of about 5 minutes. In a particular embodiment, the compound is delivered at a variable or fixed current of less than about 10 mA. In a particular embodiment, the compound is delivered for a time of less than about 10 minutes.

One embodiment is directed to a kit for iontophoretically delivering dexamethasone into the eye of a subject, wherein the kit is to be used for iontophoresis between a pH range of about 2.5 to about 6.5, and an apparatus for iontophoretically delivering the compound into the eye of a subject.

One embodiment is directed to a dexamethasone formulation suitable for ocular iontophoretic delivery into the eye of a subject. In a particular embodiment, the dexamethasone is in the form of a prodrug. In a particular embodiment, iontophoretic delivery is to be performed in a pH range of between about 2.5 and about 6.5. In a particular embodiment, the pH is about 5.7.

One embodiment is directed to a device for delivering dexamethasone, comprising: a) a reservoir comprising at least at least one medium comprising a dexamethasone formulation, the reservoir extending along a surface intended to cover a portion of an eyeball; and b) an electrode associated with the reservoir so as to, when polarized, supply an electric field directed through the medium and toward a surface of the eye, wherein at least a portion of the dexamethasone formulation is delivered transdermally through the surface of the eye through iontophoresis. In a particular embodiment, the reservoir comprises: a) a first container for receiving the at least one medium comprising the dexamethasone formulation; b) a second container for receiving an electrical conductive medium comprising electrical conductive elements; and c) a semi-permeable membrane positioned between the first and second containers, the semi-permeable membrane being permeable to electrical conductive elements and non-permeable to the active substances.

One embodiment is directed to a method for treating a corticosteroid sensitive ophthalmic disease in a mammal, comprising administering an effective amount of a corticosteroid by ocular iontophoresis. In a particular embodiment, the ophthalmic disease is selected from the group consisting of: uveitis, dry eye, post operative inflammation and corneal graft rejection. In a particular embodiment, the corticosteroid is dexamethasone phosphate. In a particular embodiment, administration of dexamethasone phosphate occurs in a single dose.

DETAILED DESCRIPTION

Figure 1:
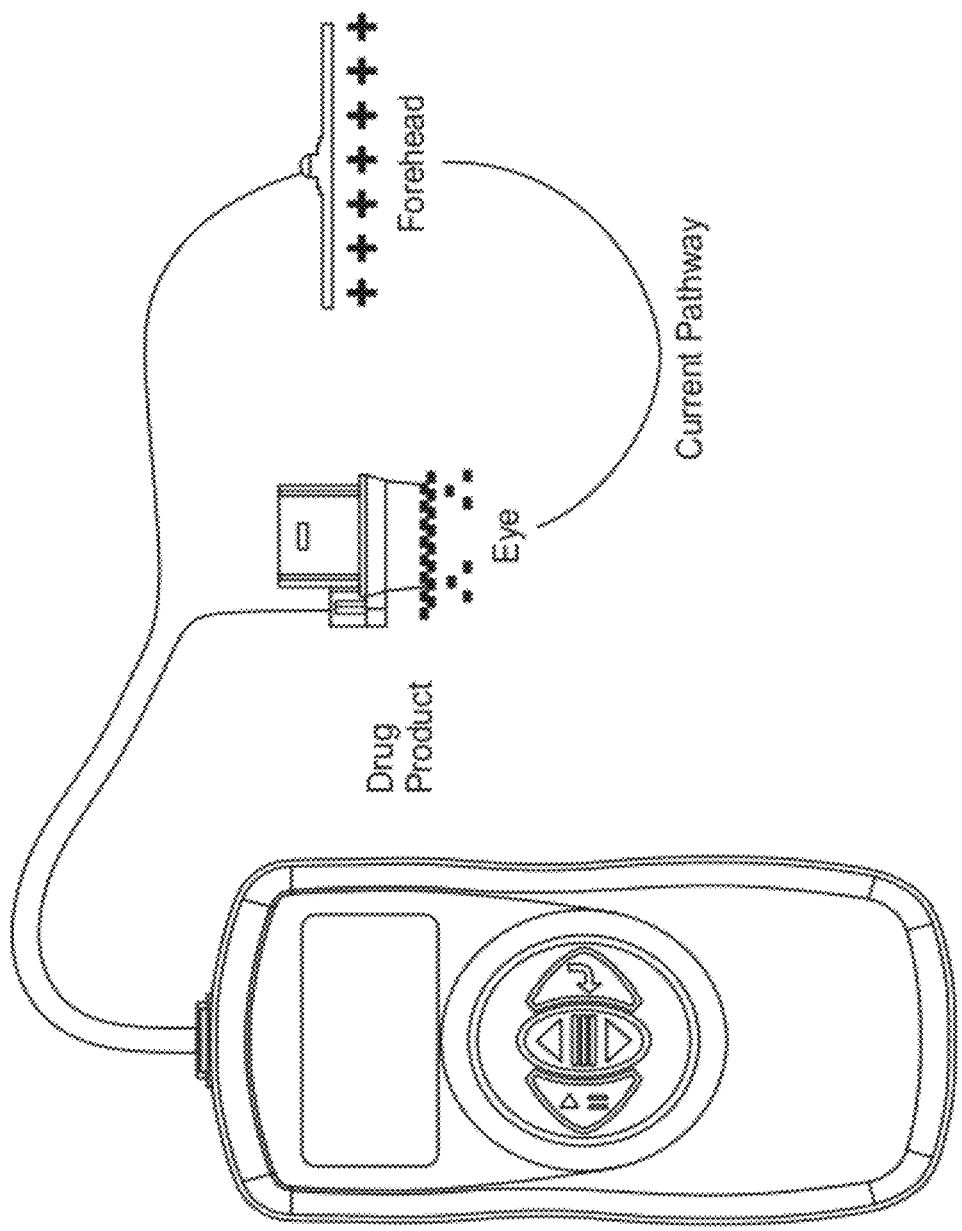
FIG. 1 is a schematic overview of the iontophoresis apparatus and procedure.

The process of iontophoresis involves applying a current to an ionizable substance, for example a drug product, to increase its mobility across a surface. Three principle forces govern the flux caused by the current. The primary force is electrochemical repulsion, which propels like charged species through surfaces (tissues). The earliest investigations of iontophoresis involve transdermal applications.

When an electric current passes through an aqueous solution containing electrolytes and a charged material (for example, the active pharmaceutical ingredient or API), several events occur: (1) the electrode generates ions, (2) the newly generated ions approach/collide with like charged particles (typically the drug being delivered), and (3) the electrorepulsion between the newly generated ions force the dissolved/suspended charged particles (the API) into and/or through the surface adjacent (tissue) to the electrode. Continuous application of electrical current drives the API significantly further into the tissues than is achieved with simple topical administration. The degree of iontophoresis is proportional to the applied current and the treatment time. Corticosteroids can be delivered at fixed or variable current settings ranging from, for example, about 1 mA to about 10 mA. The overall iontophoretic dose is a function of current and time. The iontophoretic dose, for example, can be applied over a period of less than about 10 minutes, less than about 15 minutes, less than about 20 minutes, or about 5 minutes.

Iontophoresis occurs in water-based preparations, where ions can be readily generated by electrodes. Two types of electrodes can be used to produce ions: (1) inert electrodes and (2) active electrodes. Each type of electrode requires aqueous media containing electrolytes. Iontophoresis with an inert electrode is governed by the extent of water hydrolysis that an applied current can produce. The electrolysis reaction yields either hydroxide (cathodic) or hydronium (anodic) ions. Some formulations contain buffers, which can mitigate pH shifts caused by these ions. The presence of certain buffers introduces like charged ions that can compete with the drug product for ions generated electrolytically, which can decrease delivery of the drug product. The electrical polarity of the drug delivery electrode is dependent on the chemical nature of the drug product, specifically its $pK_a(s)$/isoelectric point and the initial dosing solution pH. It is primarily the electrochemical repulsion between the ions generated via electrolysis and the drug product's charge that drives the drug product into tissues. Thus, iontophoresis offers a significant advantage over topical drug application, in that it increases drug absorption. The rate of drug delivery may be adjusted by varying the applied current, as determined by one of skill in the art.

Ocular iontophoresis has been reported in the literature, but the fundamental understanding of this approach for drug delivery, especially at the typically much higher currents used, is not at the same level as that for transdermal electrotransport. The present invention, therefore, is directed to unexpected discoveries about the formulations and conditions for using particular DEX phosphate formulations for ocular iontophoresis. In particular, electrical properties of the sclera (charge, permselectivity, pI) and the basics of iontophoretic transport of model anionic species (e.g., buffered DEX phosphate) are described.

Definitions

As used herein, the term "subject" refers to an animal, in particular, a mammal, e.g., a human.

As used herein, the term "efficacy" refers to the degree to which a desired effect is obtained. Specifically, the term refers to the degree to which dexamethasone or a prodrug thereof is effective in treating inflammation. The term "efficacy" as used in the context of the present invention, also refers to relief or reduction of one or more symptoms or clinical events associated with inflammation.

As used herein, "anterior uveitis" refers to an intraocular inflammation of the anterior portion of the uvea (i.e., the iris and ciliary body). "Iritis" refers to an inflammation of the iris only, while "iridocyclitis" involves both the iris and the ciliary body. The terms "anterior uveitis", "iritis", and "iridocyclitis" are often used synonymously. Anterior uveitis is termed "acute" when the inflammation lasts less than 12 weeks or "chronic" when it lasts longer. Chronic anterior uveitis is characterized by a duration of greater than three months and the recurrence of the disease with multiple episodes. Recurrence indicates the return of intraocular inflammation after a period of quiescence.

As used herein, "DEX" generally refers to dexamethasone compounds, derivatives and salts thereof, e.g., dexamethasone phosphate, dexamethasone sodium phosphate. As used herein, the term "derivative" can refer to a chemical modification, for example, of a corticosteroid.

As used herein, "glucocorticoids" refers to corticosteroids, often useful in treating various inflammation disorders. Glucocorticoids or corticosteroids, like dexamethasone, suppress inflammation by inhibiting, for example, edema, fibrin deposition, capillary deposition, and phagocytic migration of the inflammatory response. As in other tissues, corticosteroids do not appear to have specific effects in ocular tissues but exert a broad spectrum of anti-inflammatory activity. The effects of corticosteroids in ocular tissues include: 1) reduction of the cellular immune response, 2) reduction of inflammatory vascular permeability, 3) stabilization of the blood-aqueous barrier, 4) limitation of fibrinoid exudation, 4) inhibition of fibroblast transdifferentiation, 5) inhibition of epithelial proliferation, 6) inhibition of inflammatory corneal neovascularization, 7) retardation of wound healing, 8) elevation of intraocular pressure, and 9) induction of cataract. Corticosteroids also inhibit leukocyte movement to the inflamed site and may reduce the ability of leukocytes to remain in the inflamed areas.

Active Pharmaceutical Ingredients (APIs)

The present invention is directed to methods and formulations comprising one or more of DEX, DEX phosphate and DEX sodium phosphate. Active substances, e.g., dexamethasone and formulations thereof, are preferably present in a concentration between approximately 0.1 mg and approximately 100 mg per ml of medium.

The active substances are ionizable by themselves or are in a form that facilitates their ionization. Thus, it is possible to bond active substances to additives presenting terminating ions, such as, for example, a polymer, a dendrimer, a polymer nanoparticle or a microsphere, or a liposome (the active substance is then contained in the aqueous core and not in the wall of the liposome). Various other examples of techniques for improving active substances ionization are known in the art (Bourlais, C. et al., Prog. Retin Eye Res., 17:33-58, 1998; Ding, S., Pharm. Sci. Tech. Today, 1:323-335 1998; Lallemand, P. et al., Eur. J. Pharm. Biopharm., 56:307-318, 2003).

Methods for Treating Ocular Inflammation

Corticosteroids have unparalleled anti-inflammatory effects and rapid onset of action. Corticosteroid ophthalmic solutions have been used to treat acute inflammatory conditions in the anterior eye tissues (McGhee, C. et al., Drug Saf., 25:33-55, 2002). Two clinical studies, for example, demonstrate that topical application of a potent corticosteroid using a short-term, intensive-dosing regimen alleviates acute dry eye signs and symptoms in patients with moderate to severe keratoconjunctivitis sicca (KCS) who were unresponsive to artificial tear supplementation (Marsh, P and Pflugfelder, S., Ophthalmology, 106:811-816, 1999; Hong, S. et al., J. Ocul. Pharmacol. Ther., 23:78-82, 2007). Patients experienced dry eye signs and symptoms relief for time periods that extended significantly beyond the active dosing period, suggesting that the treatment modified the underlying causative inflammatory pathology. Topical corticosteroids remain the mainstay treatment for corneal graft rejection episodes. The pharmacological effects of steroids include blockage of the prostaglandin synthesis by inhibiting phospholipase A2 and the lipo-oxygenase pathways, decrease of both cellular and fibrinous exudation, inhibition of chemotaxis and phagocytosis, restoration of capillary permeability, stabilisation of the lysosomal membranes of polymorphonuclear cells (PMN), and inhibition of graft vascularization.

Anterior uveitis encompasses a wide range of etiologies; the most common form of anterior uveitis is of unknown etiology. The signs and symptoms of uveitis vary with etiology and location of inflammation. Anterior uveitis is differentiated from more common types of ocular inflammation by its presentation of pain or photophobia, circumlimbal redness and anterior chamber cells and flare. Patients with anterior uveitis may exhibit symptoms of pain in one eye unless the anterior uveitis is secondary to a systemic disease, in which case pain or redness is not necessarily a symptom. Common vision-threatening complications of anterior uveitis (e.g., posterior subcapsular cataract (PSC), glaucoma and macular edema) generally occur due to its recurrent nature.

Medical management of anterior uveitis depends on severity and consists of topical or systemic corticosteroid treatment and often with cycloplegics. When topical steroid drops are used, the frequency of treatment can range from every 15 to 30 minutes, to every hour, or to every other day depending on the severity of the inflammation being treated. The role of corticosteroids in treating anterior uveitis is to decrease inflammation by reducing, for example, the production of exudates, stabilizing cell membranes, inhibiting the release of lysozyme by granulocytes, and suppressing the circulation of lymphocytes. Cycloplegics serve three purposes in the treatment of anterior uveitis: 1) to relieve pain by immobilizing the iris; 2) to prevent adhesion of the iris to the anterior lens capsule (posterior synechia), which can lead to iris bombe and elevated intraocular pressure (IOP); and 3) to stabilize the blood-aqueous barrier and help prevent further protein leakage (flare).

The steroid hormone dexamethasone [9-fluoro-11β,17,21-trihydroxy-16α-methylpregna-1,4-diene-3,20-dione] belongs to the class of glucocorticoid steroid hormones that can suppress the inflammatory response to a variety of agents of mechanical/surgical, chemical, and/or immunological nature. The anti-inflammatory activity of dexamethasone administered systemically is about six to ten times greater than that of prednisone or prednisolone and about 30 to 40 times more potent than cortisone. Dexamethasone (DEX) has been shown to be effective in suppressing and/or blocking inflammation in the eye in human clinical studies and in rabbit models.

DEX is currently available in multiple commercial forms, which include some prodrugs: dexamethasone base (alcohol), acetate or disodium phosphate. DEX and its prodrugs can be administered orally, topically, by intravenous or intramuscular injection or inhaled. In ophthalmology, DEX disodium phosphate (Decadron®, Merck & Co.) 0.1% solution has been used. Although 0.1% solutions are widely used for ocular treatments, the doses and durations of treatment vary considerably across individual patients. DEX phosphate 0.1% solutions do not readily penetrate the intact cornea. Selection of the DEX dose for treatment of ocular inflammation is based mostly on clinical effectiveness data, with supportive information from pharmacology and pharmacokinetic studies.

Patients with anterior uveitis are typically treated aggressively with a potent topical steroid agent during the initial stage of inflammation, and re-evaluated at frequent intervals, with a schedule of steroid tapering dictated by clinical response, as determined by one of skill in the art. Thus, in practice, the principal means of regulating the dosage of a topically applied corticosteroid is to vary the frequency with which the medication is instilled. When a maximal effect is desired, topical steroids are administered hourly, or even more frequently. In very severe cases of anterior uveitis, prednisolone acetate 1% or dexamethasone alcohol 0.1% may be required hourly around the clock, together with periocular and/or oral corticosteroids as adjunctive therapy. Compliance with these regimens is often a consideration when treatment effectiveness is being evaluated. Most treatment failures with topical steroids are believed to be due to poor patient compliance, inadequate dosing, or abrupt or rapid tapering schedules.

In addition to uveitis, other conditions suitable for treatment by iontophoresing dexamethasone into the eye include, for example, dry eye, diabetic macular edema, age-related macular degeneration, and other inflammatory eye conditions.

Ocular Iontophoresis Apparatus

Devices for delivering, for example, dexamethasone and suitable formulations thereof, have been described (U.S. Pat. No. 6,154,671; U.S. Pub. App. No. 2006/0142706; U.S. Pub. App. No. 2005/0245856; WO 2006/072887; and U.S. Pub. App. No. 2007/0123814; the contents of each of which are herein incorporated by reference in their entireties).

In a preferred embodiment, an iontophoretic device, with a topical applicator, is used to perform ocular iontophoresis. An example of such a device is described below, however, one of skill in the art would appreciate that other devices suitable for ocular iontophoresis are useful for using the formulations and methods of the present invention.

The iontophoresis applicator is annular in shape, and designed to fit over the sclera of the eye, to allow direct delivery of drug to the eye. The inner diameter of the applicator is the same diameter as the average cornea to help facilitate the centering of the device on the eye. The active contact surface between the eye and the applicator consists of soft polyurethane hydrophilic foam; this foam serves as the reservoir for the dexamethasone phosphate solution to be delivered during treatment. The electrode is inert and annular in shape to match the shape and size of the foam.

The foam reservoir can be made of hydrophilic foam that facilitates the reservoir filling process and helps eliminate air bubbles in the system. The distal part of the applicator and the foam reservoir of the applicator function as the interface between the eye and the device. The dimensions of these components are specifically designed to fit over the sclera, 1 mm from the limbus. The inside diameter of the applicator serves as a viewing port to aid in placement and centration of the applicator.

The dimensioning and shape of the reservoir is such that the molecules to be delivered are distributed in a homogeneous manner and on the large ocular area so as to minimize their action per area unit, and thus to preserve the superficial ocular tissue from too much stress, and also to deliver the produce precisely in targeted intraocular tissues with avoiding systemic absorption. A larger surface area allows a lower electric field resident time on the eyeball and limits the current density on it.

The application, surface of the reservoir can be chosen for covering a target area. It is thus not only the surface area, but also the shape of the reservoir that can be adapted for reaching the purpose of maximizing a homogeneous distribution of active substances. The reservoir of the device, for example, can be adapted to administer the active substances via at least a part of the cornea alone, or at least a part of the sclera and at least a part of the cornea, or at least a part of the sclera alone. In some embodiments, the application surface of the reservoir is annular and capable of extending around the optical axis of the eyeball.

The medium housed in the reservoir extends from a surface of the eyeball. The medium can include, for example, a natural or synthetic gel member, a natural or synthetic foam that is geometrically and compositionally compatible for ocular applications for receiving the active substances in solution, or a single solution. Electrically-conductive media, such as, for example, water or hydrogel, can also be placed in the reservoir to guide and conduct the electric field through the reservoir to the surface of the eyeball. The medium can also contain supplemental agents, such as, for example, electrolytes, stability additives, medicament preserving additives, pH regulating buffers, PEGylating agents and any other agent that, when associated, increase the half-life and/or bioavailability.

The applicator electrode can be made of, for example, a flat film with a silver coating on one surface and a conductive carbon coating on the other surface. The silver coated surface of the electrode is in contact with the source connector pin and helps disperse the current evenly around the electrode. The conductive carbon is in contact with the drug product in the foam reservoir and serves to transfer the current to the drug product; the carbon surface is inert and does not react with the drug product. The electrode is, for example, about 6 mm away from the surface of the eye to minimize any potential thermal effects from the applicator electrode.

A passive or return electrode can be placed on a portion of the body (to "loop" current through the body), for example on an ear, the forehead or a cheek. As with the active electrode, the passive electrode can include an anode or a cathode depending upon whether the active substances are cationic or anionic. The return electrode can be very similar to, for example, a standard TENS type electrode. It consists of multiple layers of conductive materials that are designed to allow the current to pass out from the patient and back to the constant current generator. The electrode is flat, rectangular in shape and sized to fit on the forehead. A commercially-available conductive gel adhesive secures the electrode to the patient.

The active, or applicator electrode, can be advantageously arranged, in operation, to present current density of about 10 mA/cm² or less, and to be polarized for about ten minutes or less. In some embodiments, the device includes a protective layer optionally formed on a surface of the active electrode so as to protect it or to protect the inactive substances from metallic contaminants, as described in PR 04/04673, the contents of which are herein incorporated by reference in its entirety. The device can be advantageously arranged in such a manner that the distance between the active electrode and the ocular surface is chosen to prevent any damage of the ocular tissue due to the electric field. A distance from the ocular surface to the active electrode can be chosen, for example, to be at least about 4 mm.

The transfer system can be comprised of a syringe and spike, serving to transfer the drug product from a standard vial to the foam reservoir of the applicator. The spike, which can be fabricated from plastic, has a sharp end that is used to perforate the top seal of the glass vial containing the DEX phosphate ophthalmic solution. The distal end of the transfer system mates with the applicator to facilitate the transfer of drug product from the syringe to the applicator reservoir. Alternatively, the transfer system can be provided as a sterile, single-use, disposable product.

The iontophoresis generator can be a hand held battery operated device designed to deliver a constant current to the applicator in the predetermined range used for iontophoretic delivery of the drug product. The generator automatically ramps up the current at a predetermined rate to the desired current, as determined by one of skill in the art.

Iontophoresis Parameters

Several interdependent factors influence the overall efficacy and safety of a particular topical steroid preparation in the treatment of ocular inflammatory disease. These include the ability of a topical steroid to penetrate through the cornea, sclera or blood-ocular barrier, relative anti-inflammatory potency and duration of action, the dose and frequency of administration and the adverse event profile. Given the medical imperative to intervene early and aggressively in eyes with, for example, anterior uveitis, and the high frequency of administration required to achieve adequate therapeutic levels of steroid in the anterior chamber, alternative methods of steroid delivery into the eye are of clinical interest.

Described herein are pertinent solution parameters that produce a DEX sodium phosphate formulation effective for delivery by ocular iontophoresis. Both the upper and lower effectiveness limits of each parameter are described, and one of skill in the art would know how to adjust these parameters to produce, for example, a controlled rate of drug delivery. The parameters considered are as follows:

1. pH This is measured by a calibrated pH meter. Various pH ranges are obtained by pH adjustment with acid or base using various buffering systems including, for example, phosphate buffers,
2. Conductivity This is measured by a calibrated pH/conductivity meter. Various conductivity ranges are obtained by altering the salt (e.g., NaCl, KCl, etc.) concentration.
3. Osmolarity. This is measured by a calibrated osmometer. Various osmolarity ranges are obtained by addition of, for example, mannitol.
4. Ionic Strength Various ionic strengths are obtained by the addition of various ionic compounds (e.g., NaCl, KCl, CaCl₂, MgCl₂, etc.). Ionic strength is determined by using the following calculation:

$$I = \frac{1}{2}\sum C_i z_i^2$$

where I is ionic strength. $C_i$ is the concentration of the $i^{th}$ molecule, and $z_i$ is the charge of the $i^{th}$ molecule.

5. Viscosity This is measured by a calibrated viscometer. Various viscosities are obtained by the addition of, for example, various polyethylene glycol species (PEG's).

Other parameters that are considered in optimizing delivery of DEX include, for example, use of inert versus active electrodes, choice of buffer system, choice of excipient (possibly required for adjusting osmolarity), compound charge (e.g., $pK_a$ and pI), compound solubility, API concentration, compound stability, choice of drug stabilizer, co-solvents and emulsions.

The applicator used to deliver the drug formulation utilizes an electrode (inert or active) that stimulates the electrolysis of water to produce ions (hydroxide or hydronium), which are required to deliver charged molecules. An anion at physiological pH, cathodic delivery (generating hydroxide ions), therefore, is required to deliver DEX phosphate. This process generates hydroxide ions that promote movement of the anionic DEX phosphate into the ocular tissues, and concurrently raises the pH of the drug solution. The drug product solution offers sufficient buffering capacity to accommodate all hydroxide ions generated with dosing. The unique physicochemical properties of DEX phosphate, specifically the two pKa's of DEX phosphate, allow the production of a highly water soluble formulation with significant buffering capacity.

An aqueous formulation of DEX would not be suitable for ocular iontophoresis because DEX lacks a charged group and has very limited aqueous solubility (0.1 mg/mL). These two shortcomings are overcome by utilizing the prodrug of dexamethasone, e.g., dexamethasone phosphate, which offers an additional advantage, internal buffering capacity. The finished drag product intended for iontophoretic delivery in patients with anterior uveitis is an aqueous solution of DEX phosphate (at a concentration of about, for example, 40 mg/mL, between about 25 and 50 mg/mL; and between about 10 and 100 mg/mL) produced by methods known in the art (e.g., by suspending the API in water for injection and then adjusting the pH of the solution to 5.7 with sodium hydroxide). As the solution becomes less acidic, DEX phosphate dissolves, resulting in a clear solution. In one embodiment, the finished drug product can be filter sterilized and aseptically filled into USP Type 1 glass vials. The vials can be closed with, for example, bromobutyl rubber stoppers and an aluminum overseal. The vials of finished drug product can be stored at about 2-8° C., protected from light. The product can be warmed to room temperature prior to administration.

EXEMPLIFICATION

Example 1

Conditions for Ocular Iontophoresis of DEX

In vitro testing was performed at ±3 mA using a 10 mg/mL solution in 100 mM sodium citrate at pH~5.66. Approximately 1% transferred to receptor using cathodic delivery.

Figure 2:
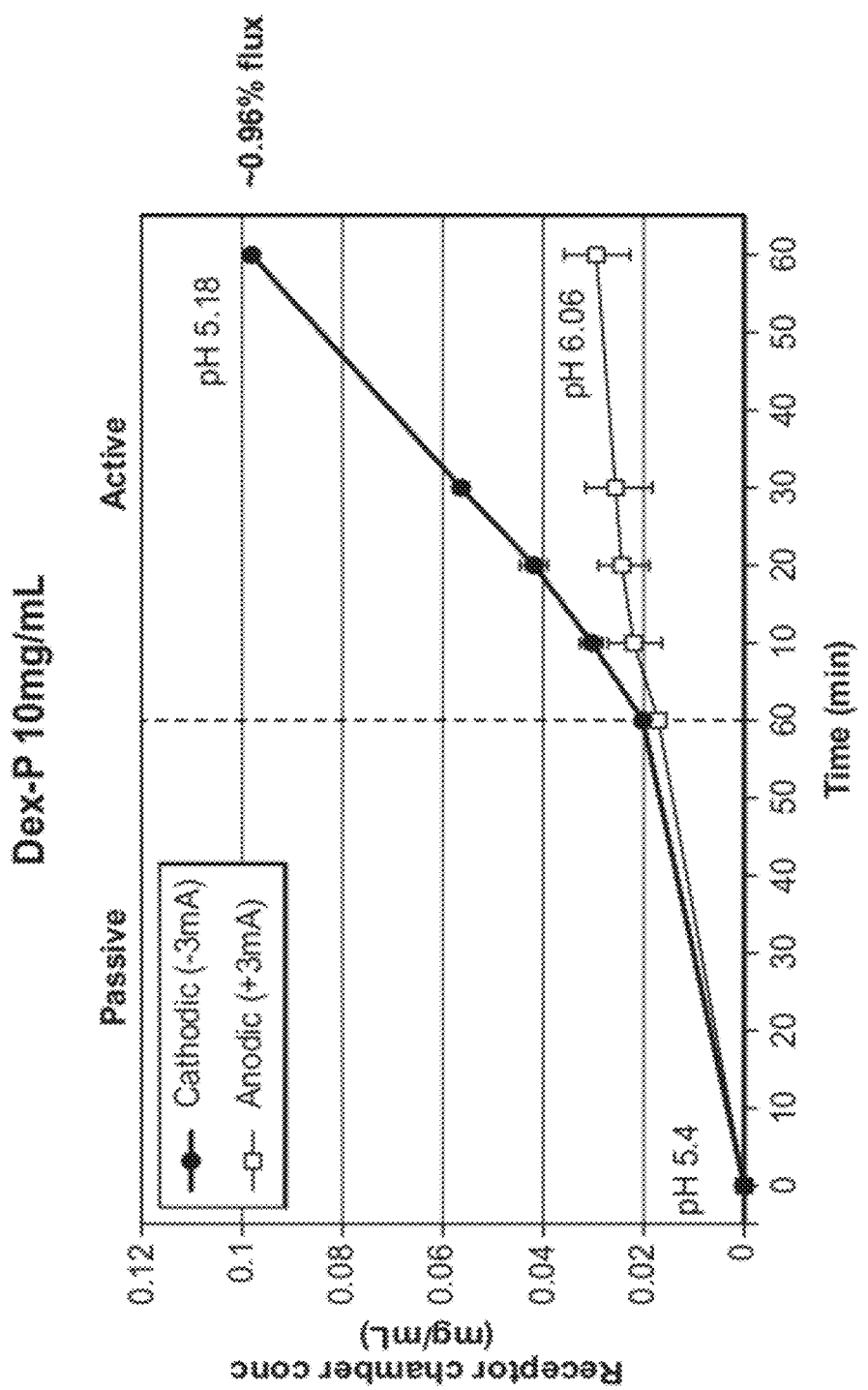
FIG. 2 is a graph showing in vitro delivery of DEX phosphate.
Figure 3:
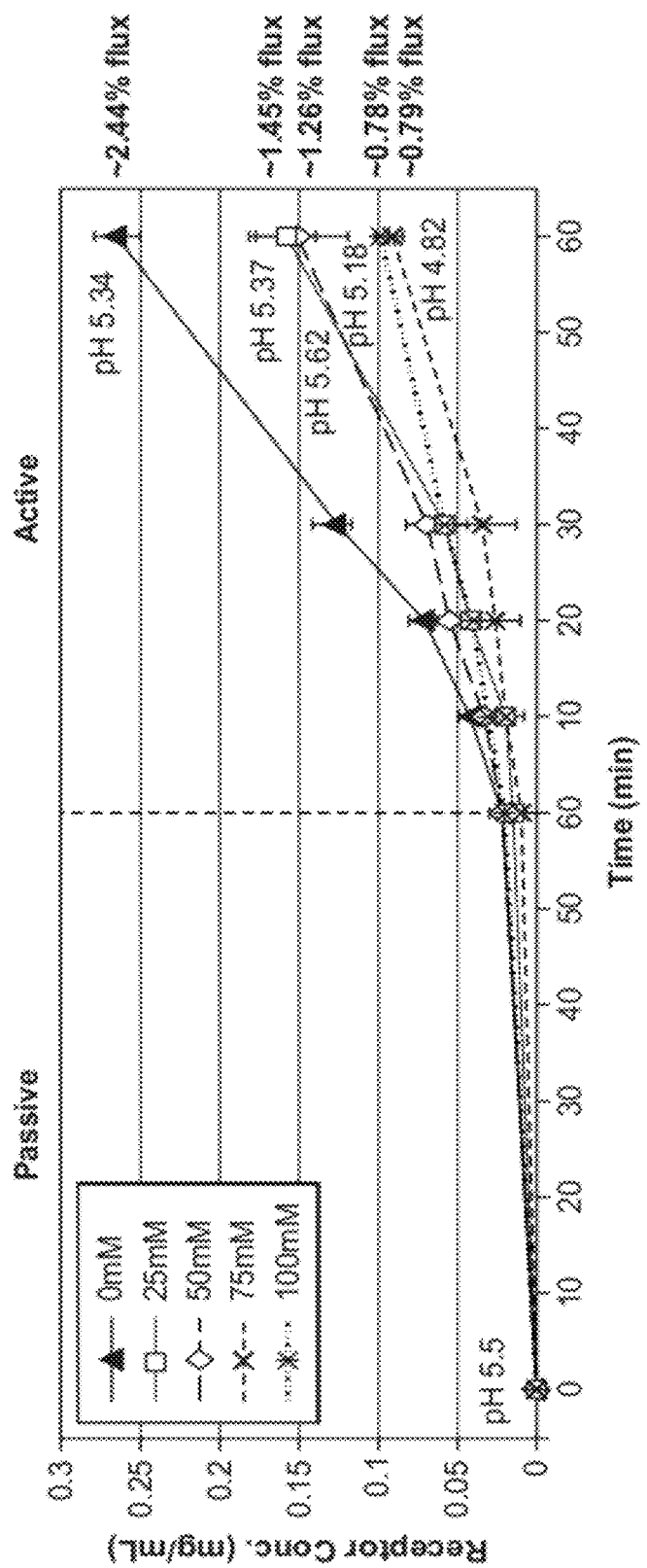
FIG. 3 is a graph showing in vitro delivery of DEX phosphate using varying sodium citrate concentrations.

In vitro testing was performed using four different concentrations of sodium citrate buffer to examine the effect of reducing the number of competing ions on transport efficiency of DEX. Decreasing the amount of sodium citrate increased DEX flux (see FIGS. 1 and 2).

Other conditions are varied including, for example, eliminating the pH change from the lower concentrations of sodium citrate solutions and using various non-charged excipients to modulate the donor solution osmolarity.

Example 2

DEX Electrotransport Across Rabbit Sclera with an Inert Electrode

Described herein is a study of ocular iontophoresis: specifically, a characterization of the barrier's permselectivity and to establish structure-transport relationships. The electrotransport of model anionic compounds (DEX phosphate) has been examined across rabbit sclera. DEX phosphate, a widely used ophthalmic drug, was chosen as model negatively-charged agent. It is a further goal to examine whether drug flux across the sclera can be optimized using the same strategies that have proven successful for skin and, in particular, to confirm that linear "flux-current" relationships also apply at the higher current densities used in ocular delivery.

Methods

All transscleral iontophoresis studies were performed in side-by-side diffusion cells (transport area=0.2 cm$^2$, volume=4 mL) with excised rabbit sclera. The tissue was freed from the conjuctiva, extraocular muscles and retina. The sclera was clamped between the two half-cells, with the conjunctival side facing the drug solution. Pt or Ag/AgCl electrodes were used to deliver the constant current, which was provided by a power supply. Each experiment was performed in at least quadruplicate. Appropriate passive, no-current controls were performed.

Cathodal trans-scleral iontophoresis of DEX phosphate was conducted at 0.5, 1, and 2 mA for 2 hours. The donor solution was 0.4% w/v DEX phosphate in water. The receptor solution was again phosphate-buffered saline at pH 7.4. A limited number of experiments were also carried out, in this instance, using sheep sclera. The data from these studies were indistinguishable from those obtained using the corresponding rabbit membranes. Samples of the receptor phase were assayed for dexamethasone by HPLC.

Results

Figure 4:
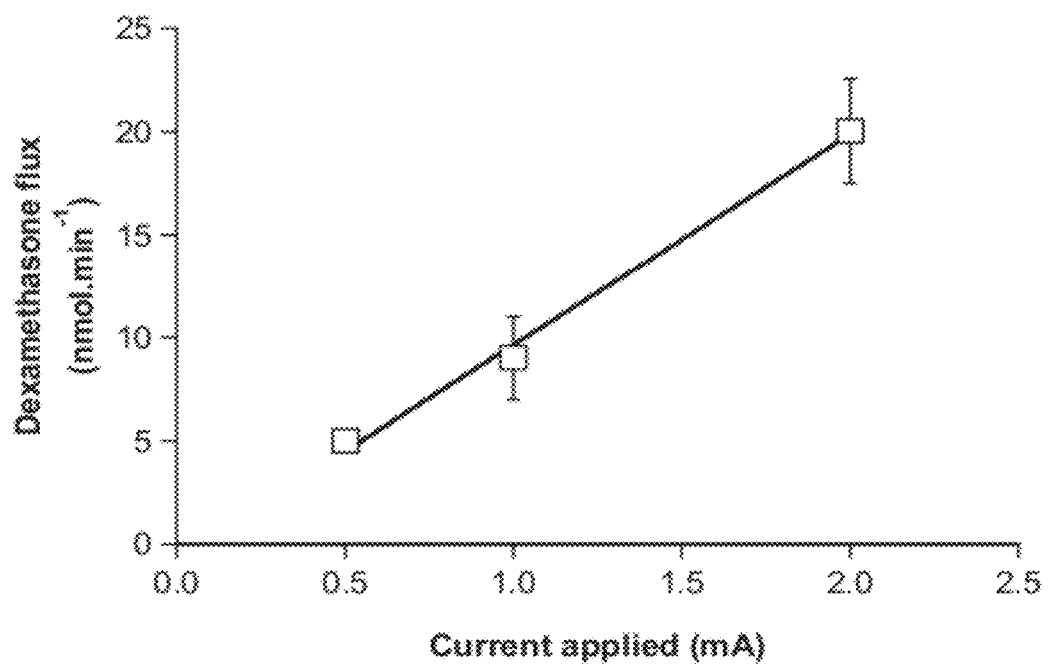
FIG. 4 is a graph showing linear dependence of DEX phosphate flux on applied current (mean±SD, n=4).

Iontophoretic delivery of dexamethasone phosphate across the sclera was facile, and the fluxes achieved after one hour were directly proportional to the applied current (FIG. 4).

Example 3

Testing was performed using dexamethasone and the two prodrugs, DEX sodium phosphate and DEX phosphate. Based on comparative pharmacokinetic data, DEX phosphate was selected as a suitable prodrug for iontophoretic delivery. Since dexamethasone is considered to be the active moiety of the prodrugs, this section describes the pharmacology of dexamethasone.

Published literature supports the pharmacologic effect of dexamethasone, particularly in models of ocular inflammation. A number of experiments have been reported that characterize the pharmacologic effects of dexamethasone, both in vitro and in vivo. Often prodrugs of dexamethasone are used in these pharmacology studies, and it is assumed that the conversion of these prodrugs to dexamethasone occurs relatively rapidly and completely. These combined data support that dexamethasone efficiently and effectively inhibits inflammation. The in vitro and in vivo studies leading to these findings are described herein.

Described herein are formulations and methods for delivering DEX to a subject. The iontophoretic delivery of therapeutic agents into the eye is of interest as a means of non-invasively achieving higher drug levels inside the eye by promoting the movement of charged substances (drug products) across biological membranes by applying a low electrical current forming an electrical field. The electric field causes electrorepulsions between the newly formed ions and the drug product, which propels the drug product into ocular tissue. The iontophoretic delivery of an aqueous dosing solution of dexamethasone phosphate, an anion at physiological pH, requires cathodic electrolysis with, for example, an inert electrode. This process generates hydroxide ions that promote movement of the anionic dexamethasone phosphate into the ocular tissues, while concurrently raising the pH of the drug product solution. The unique physicochemical properties of DEX phosphate, specifically the two pKa's (1.9 and 6.4) of dexamethasone phosphate, however, allow the production of a highly water soluble formulation (40 mg/mL) with significant buffering capacity (initial pH 5.7-5.8) to accommodate hydroxide ions generated.

The biophysical and biological mechanisms responsible for the tissue penetration of active products are not well understood. Most transdermal models are based on the modified Nernst-Planck equation. According to this equation, total flux is the sum of active and passive transport mechanisms: passive diffusion, electrorepulsion, and electroosmosis flux, which are summarized in the Nernst-Planck equation below:

$$Flux_{total} = Flux_{passive} + Flux_{electric} + Flux_{osmotic}$$

$$FLUX_{TOTAL} = -D/(DC/DX) + (D.Z.V.F.C_i)/(K.T) \pm C.U$$

where:
D=Diffusion coefficient (characteristic of the biological membrane)
dc/dx=Concentration gradient
z=valence
V=Electrical field
F=Faraday's constant
K=Boltzmann's constant
T=Temperature
$C_i$=Ionized drug concentration
C=Drug concentration
u=convective flow of water In Vitro Testing In vitro experiments were conducted to evaluate drug product stability under iontophoresis. These experiments employed Ussing chambers, using a wide range of iontophoretic doses (e.g., up to 120 mA·min). Compound concentrations were measured using HPLC analysis coupled to a UV detector, and standard curves were generated by testing solutions at various concentrations.

The donor and receiving chambers are connected by a ball and socket joint with freshly harvested rabbit scleral tissue compressed into the joint (using the cell clamp and tension knob). A 40 mg/mL aqueous DEX phosphate solution (pH adjusted to 5.7 with 1.0 N aqueous sodium hydroxide) was placed in the donor chamber. The receiving chamber was filled with 0.9% saline. After standing at room temperature for up to 120 minutes, samples were removed from the donor and accepting chambers to appraise DEX phosphate and dexamethasone concentrations. Next, inert electrodes were placed into the donor and acceptor chambers. The connecting wires were configured at the generator in order to produce cathodic iontophoresis. At a variety of time points, aliquots were removed from the donor and receiving chambers in order to quantify dexamethasone, dexamethasone phosphate, and any impurities. On average, little or no dexamethasone/dexamethasone phosphate was transferred passively (without current) and up to 5% of the material was fluxed across the membrane (with current). For up to 120 minutes, no significant impurities were detectable in the donor or receiving chambers. A linear proportional drug product concentration relationship was obtained.

Approximately 95% of the original DEX phosphate concentration was present in the donor chamber. The residual solution contained one quantifiable material (concentration >0.5%). The quantifiable material represented <5% of the total area under the curve based on HPLC (UV detection), which was dexamethasone (based on comparison to a reference standard). No other quantifiable materials were detected.

The receptor chamber contained <5% of the total DEX phosphate that was present at the beginning of the study in the donor chamber. Within the receptor chamber solution, 95% of the material was dexamethasone phosphate. The balance of the material, which represented <5% of the total area under the curve based on HPLC (UV detection), was dexamethasone (based on comparison, to a reference standard). No other quantifiable materials were detected.

Absorption and Ocular Tissue Concentrations

The ocular tissue concentrations of DEX phosphate (the prodrug) and dexamethasone (active moiety) two hours after topical administration, subconjunctival injection and constant coulomb iontophoresis delivery of DEX disodium phosphate were evaluated in 42 male and female Fauve de Bourgogne pigmented rabbits (6/group). The seven treatments were single doses administered to the right eye as follows;

Group 1: Iontophoretic device placed on right eye loaded with Sterile Water for Injection; no current was applied;

Group 2: Iontophoretic delivery of DEX disodium phosphate with iontophoretic device at 2.5 mA for 5 minutes (device loaded with 0.5 mL of DEX disodium phosphate 10 mg/mL solution, Sigma)

Group 3: Iontophoretic delivery of DEX disodium phosphate with iontophoretic device 2.5 mA for 5 minutes (device loaded with 0.5 mL of DEX disodium phosphate 40 mg/mL solution, Sigma)

Group 4: Iontophoretic delivery of DEX disodium phosphate with iontophoretic device 2.5 mA for 5 minutes (device loaded with 0.5 mL of DEX disodium phosphate 10 mg/mL solution, Abraxis)

Group 5: Subconjunctival injection of DEX disodium phosphate (0.75 mL of DEX disodium phosphate 40 mg/mL solution, Sigma)

Group 6: Subconjunctival injection of DEX disodium phosphate (0.75 mL of DEX disodium phosphate 10 mg/mL solution, Abraxis)

Group 7: Topical instillation of DEX disodium phosphate (0.05 mL of DEX disodium phosphate 10 mg/mL solution, Abraxis)

Ocular tissues and plasma collected 2 hours post dosing were analyzed for DEX phosphate and dexamethasone concentration. Samples were analyzed by an ELISA or HPLC-MS/MS method. Iontophoresis or subconjunctival administration provided higher ocular tissue concentrations of DEX phosphate and dexamethasone compared to topical instillation. Subconjunctival administration resulted in very high concentrations of DEX phosphate and dexamethasone in conjunctiva and choroid tissue. Other ocular tissues had high levels of dexamethasone and DEX phosphate. Aqueous humor concentrations correlated with iris-ciliary body tissue concentrations two hours post dose for all dosing modalities investigated. Vitreous humor concentrations correlated with retina concentrations two hours post dose of all dosing modalities. Systemic exposure at two hours post dosing was very low (<100 ng/mL) for iontophoresis and topical administration of DEX disodium phosphate. Subconjunctival administration resulted in low but measurable plasma levels (<4000 ng/mL) at two hours post dose.

The pharmacokinetics of dexamethasone and DEX phosphate after iontophoretic administration by the iontophoretic device were characterized in 24 female New Zealand White rabbits. Dexamethasone phosphate (60 mg/mL) was administered iontophoretically at 3 mA for 5 minutes as a single dose to both eyes or DEX phosphate 40 mg/mL was iontophoretically delivered once daily for 3 consecutive days to both eyes. Ocular tissues and plasma were analyzed for DEX phosphate and dexamethasone concentrations by an HPLC-MS/MS method in serial samples collected post dosing. Dose proportional increases in plasma and ocular tissue concentrations and exposure measures of dexamethasone were observed after iontophoretic administration of the 40 mg/mL versus 60 mg/mL DEX phosphate solution (Table 1).

TABLE 1

| | Single Dose-40 mg/mL Dex P | | Single Dose-60 mg/mL Dex P | |
|---|---|---|---|---|
| Ocular Tissue or Plasma | Dex $AUC_{0-6\,h}$ (µg · h/g or µg · h/mL) | Dex $AUC_{0-24\,h}$ (µg · h/g or µg · h/mL) | Dex $AUC_{0-6\,h}$ (µg · h/g or µg · h/mL) | Dex $AUC_{0-24\,h}$ (µg · h/g or µg · h/mL) |
| Aqueous Humor | 56.5 | 73.8 | 123 | 132 |
| Vitreous | 1.5 | 2.2 | 2.3 | 3.0 |
| Choroid | 24.9 | 35.9 | 49.5 | 66.7 |
| Plasma | 1.6 | 3.3 | 3.7 | 6.6 |

| | Single Dose-40 mg/mL Dex P | | Single Dose-60 mg/mL Dex P | |
|---|---|---|---|---|
| Ocular Tissue or Plasma | Dex $C_{max}$ (µg/g or µg/mL) | Dex $T_{max}$ (hours) | Dex $C_{max}$ (µg/g or µg/mL) | Dex $T_{max}$ (hours) |
| Aqueous Humor | 16.6 | 2 | 40.5 | 2 |
| Vitreous | 0.360 | 2 | 0.657 | 2 |
| Choroid | 7.43 | 0.25 | 12.5 | 0.25 |
| Plasma | 0.342 | 0.25 | 0.997 | 2 |

Dex P = Dexamethasone Phosphate;
Dex = Dexamethasone;
AUC = area under the concentration-time curve over a specified time period;
$T_{max}$ = time to maximum concentration;
$C_{max}$ = maximum concentration Peak dexamethasone concentrations in ocular tissues or plasma occurred relatively rapidly, within two hours post iontophoretic dosing. Significant ocular tissue concentrations of dexamethasone occurred up to six hours post iontophoretic dosing. In general, dexamethasone and DEX phosphate were nearly completely cleared from plasma and ocular tissues within 48 hours after iontophoretic administration. The choroid tissue concentration did not decline as rapidly as that of the other ocular tissues. While choroid tissue concentrations of dexamethasone and DEX phosphate were measurable at 48 hours post iontophoretic delivery of DEX phosphate, they were generally less than 10% of peak choroid concentrations. Compared to peak concentrations of dexamethasone and DEX phosphate, plasma and ocular tissue concentrations were relatively low at 24 hours post iontophoretic administration. At 24 hours post dosing, ocular tissues and plasma concentrations were less than 10% of peak dexamethasone or DEX phosphate concentrations in all tissues except for the choroid. Dexamethasone and DEX phosphate concentrations in aqueous humor correlated with concentrations in the iris-ciliary body.

The effect of pH and chemical form of DEX phosphate on dexamethasone and DEX phosphate plasma and ocular tissue concentrations after delivery by constant coulomb iontophoresis was evaluated in 6 female New Zealand White rabbits. The treatments included DEX phosphate 40 mg/mL pH 5.8 made from DEX phosphate free acid, DEX phosphate 40 mg/mL pH 5.8 made from DEX phosphate disodium salt, and DEX phosphate 40 mg/mL pH 7.0 made from DEX phosphate disodium salt. A single iontophoretic dose of 2.5 mA for 5 minutes was administered. Dexamethasone concentrations in plasma and ocular tissues were higher after iontophoretic delivery of DEX phosphate formulations prepared from DEX phosphate free acid when compared to formulations prepared from DEX phosphate disodium salt.

TABLE 2

| | | | |
|---|---|---|---|
| EVALUATION OF TOPICAL, SUBCONJUNCTIVAL INJECTION AND CONSTANT COULOMB IONTOPHORESIS DELIVERY OF DEXAMETHASONE DISODIUM PHOSPHATE IN FAUVE DE BOURGOGNE RABBITS | RABBITS/FAUVE DE BOURGOGNE/42 M&F 6/GROUP | STERILE WATER IN DEVICE; NO CURRENT; SIGMA DEX DISODIUM P 10 MG/ML AND 40 MG/ML IONTOPHORETIC DOSE OF 2.5 MA FOR 5 MIN; ABRAXIS, DEX DISODIUM P 10 MG/ML, IONTOPHORESIS 2.5 MA FOR 5 MIN; ABRAXIS DEX DISODIUM P 10 MG/ML, TOPICAL; ABRAXIS DEX DISODIUM P 10 MG/ML AND SIGMA DEX DISODIUM P 40 MG/ML SUBCONJUNCTIVAL INJECTION; SINGL DOSE TO RIGHT EYE. | DEX-P AND DEX CONCENTRATIONS AT T = 2 HOURS DETERMINED IN OCULAR TISSUES AND PLASMA IONTOPHORESIS OR SUBCONJ. DOSING PROVIDE HIGHER TISSUE CONCENTRATIONS OF DEX-P + DEX IN ALL TISSUE COMPARED TO TOPICAL INSTILLATION. SUBCONJUNC. DOSING RESULTED IN VERY HIGH CONCENTRATIONS OF DEX-P AND DEX IN CONJUNCTIVA AND CHOROID TISSUE. AQUEOUS HUMOR CONCENTRATIONS CORRELATE WITH IRIS-CILIARY BODY TISSUE CONCENTRATIONS 2 H POST DOSE FOR ALL TESTED DOSING MODALITIES. VITREOUS HUMOR CONCENTRATIONS CORRELATE WITH RETINA CONCENTRATIONS 2 H POST DOSE OF ALL TESTED DOSING MODALITIES. SYSTEMIC EXPOSURE IS VERY LOW FOR IONTOPHORESIS AND TOPICAL DOSES. SUBCONJUNC. DOSING RESULTED IN LOW BUT MEASURABLE PLASMA LEVELS AT 2 H. |
| EVALUATION OF THE PK CURVE OF DEXAMETHASONE PHOSPHATE ADMINISTERED BY CONSTANT COULOMB IONTOPHORESIS USING THE EYEGATE II DEVICE IN NEW ZEALAND RABBITS | RABBITS/NEW ZEALAND WHITE/ 24 F | DFX-P 40 MG/ML AND 60 MG/ML DOSE: 3 MA FOR 5 MIN SINGLE DOSE OR ONCE A DAY FOR 3 CONSECUTIVE DAYS TO BOTH EYES. | DOSE PROPORTIONAL INCREASES IN PLASMA AND OCULAR TISSUE CONCENTRATIONS AND EXPOSURES WERE OBSERVED AFTER IONTOPHORETIC ADMINISTRATION OF THE 40 MG/ML VERSUS 60 MG/ML DEXAMETHASONE PHOSPHATE SOLUTION. DEX AND DEX-P WERE NEARLY COMPLETELY CLEARED FROM PLASMA AND OCULAR TISSUES 48 H AFTER IONTOPHORETIC ADMINISTRATION. DEX AND DEX-P CONCENTRATIONS WERE VERY LOW AFTER 24 H IN PLASMA AND OCULAR TISSUES. DEX CONCENTRATIONS IN AQUEOUS HUMOR CORRELATE WITH CONCENTRATIONS IN IRIS-CILIARY BODY TISSUE. |

TABLE 2-continued

| EFFECT OF PH ON DELIVERY OF DEXAMETHASONE PHOSPHATE BY CONSTANT COULOMB IONTOPHORESIS USING EYEGATE II DEVICE IN NEW ZEALAND RABBITS | RABBITS/NEW ZEALAND WHITE/6 F | DEX-P 40 MG/ML PH 5.8 FROM DEX-P FREE ACID, DEX-P 40 MG/ML PH 5.8 FROM DEX-P DISODIUM SALT DEX-P 40 MG/ML PH 7.0 FROM DEX-P DISODIUM SALT DOSE: 2.5 MA FOR 5 MIN SINGLE DOSE. | DEX CONCENTRATIONS IN PLASMA AND OCULAR TISSUES WERE HIGHER AFTER IONTOPHORETIC DELIVERY OF DEX-P FORMULATIONS PREPARED FROM DEX-P FREE ACID WHEN COMPARED TO FORMULATIONS PREPARED FROM DEX-P DISODIUM SALT. |
|---|---|---|---|

Example 4

Additional parameters for iontophoretic delivery are varied. Conditions include, for example, the following:
Use of active or inert electrodes;
Varying osmolarity (typically from about 200-240 mOsm/L);
Varying the starting pH from about 2.5 to about 6.5 (typically from about 5.7-5.8);
Buffer: none or use of buffering systems known in the art;
Choice of excipient;
Drug product concentration (typically about 40 mg/mL);
Choice of drug product stabilizer: none (in cases where a stabilizer can be an irritant), or other stabilizer known in the art (see below);
Varying co-solvents; and/or
Varying emulsions Other conditions are also varied to optimize iontophoretic delivery, for example, osmolarity can range from, for example, about 200-600 mOsm/L, from about 250-500 mOsm/L, from about 300-400 mOsm/L, or from about 200-550 mOsm/L. One of skill in the art would know how to vary osmolarity to achieve optimized results.

The starting pH, typically about 2.5-7.5 can also be varied within this range to achieve optimized results, for example, a range of about 3.0-6.5, about 3.5-6.0, about 4.0-6.0, or about 5.0-6.0 can be used.

One of skill in the art would know how to vary the buffer system used to achieve a particular pH range. Exemplary buffer systems include, for example, lithium, sodium, potassium acetate, citrate, tartrate, etc.

One of skill in the art would know how to vary the choice of excipient, which could be used to adjust osmolarity, for example, by using non-charged sugars.

One of skill in the art will recognize that conditions will vary based on parameters such as, for example, the $pK_a$ of the compound to be delivered, the compound solubility, the concentration of the compound to be delivered (for example, for dexamethasone, from about 1-100 mg/mL, about 5-80 mg/mL, about 10-50 mg/mL, or from about 20-50 mg/mL).

Examples of conditions include, for example, the following:
A.
  Electrode: Inert
  Device: EyeGate II applicator
  Current pole: cathodic
  Current range: 0.01-10 mA
  Dose time: 1 second-10 minutes
  Total iontophoretic dose (current×time in minutes): 0.01-100 mAmin
B.
  Electrode: Inert
  Device: EyeGate II applicator
  Current pole: cathodic
  Current range: 0.1-10 mA
  Dose time: 30 seconds-10 minutes
  Total iontophoretic dose (current×time in minutes): 0.1-100 mAmin
C.
  Electrode: Inert
  Device: EyeGate II applicator
  Current pole: cathodic
  Current range: 0.5-10 mA
  Dose time: 30 seconds-5 minutes
  Total iontophoretic dose (current×time in minutes): 0.5-50 mAmin Preferred DEX formulations include, for example:
A.
  Electrode: Active and inert
  Osmolarity: 200-600 mOsm/L
  Starting pH: 3.5-8.5
  Vehicle: water for injection
  Stabilizers: benzyl alcohol, benzalkonium chloride, EDTA, Citrate, Bisulfite, Metabisulfite
  Concentration: 1-100 mg/mL
  Storage: aerobic and anerobic
B.
  Electrode: Inert
  Osmolarity: 200-400 mOsm/L
  Starting pH: 5.4-6.4
  Vehicle: water for injection
  Stabilizers: 0.1% benzyl alcohol, 0.01% benzalkonium chloride, 0.1% EDTA, 0.65% Citrate, 0.1% Bisulfite, 0.1% Metabisuliite
  Buffer: lithium, sodium, potassium acetate, citrate, tartrate, etc
  Choice of excipient: non-charged sugars
  Concentration: 1-60 mg/mL
  Storage: aerobic and anerobic
C.
  Electrode: Inert
  Osmolarity: 200-300 mOsm/L
  Starting pH: 5.7-6.1
  Vehicle: water for injection
  Concentration: 40 mg/mL Example 5

Single-Dose Treatment with Dexamethasone Phosphate Resolves Concanavalin A-Induced Dry Eye in Rabbits Current treatment options for dry eye include long-term treatment with artificial tears, topical corticosteroids such as prednisolone, and punctal plugs, which may result in immediate effects. These treatments can be combined with topical cyclosporine A (Restasis®), which can take up to six months to improve symptoms. Daily, multiple doses of topical corticosteroids are required for effectiveness. Long-term dexamethasone treatment, however, can have negative effects such as elevated intraocular pressure. The efficacy of a single iontophoretically-delivered dexamethasone phosphate (Dex-P) in rabbits with concanavalin A-induced dry eye was assessed.

Induction of Dry Eye in Rabbits

300 µg of Concanavalin A (Sigma) in 30 mL of phosphate-buffered saline (PBS) or PBS alone were injected into the lacrimal glands of white New Zealand rabbits to induce inflammation leading to dry eye symptoms, which is a well-established model of dry eye syndrome.

Figure 5:
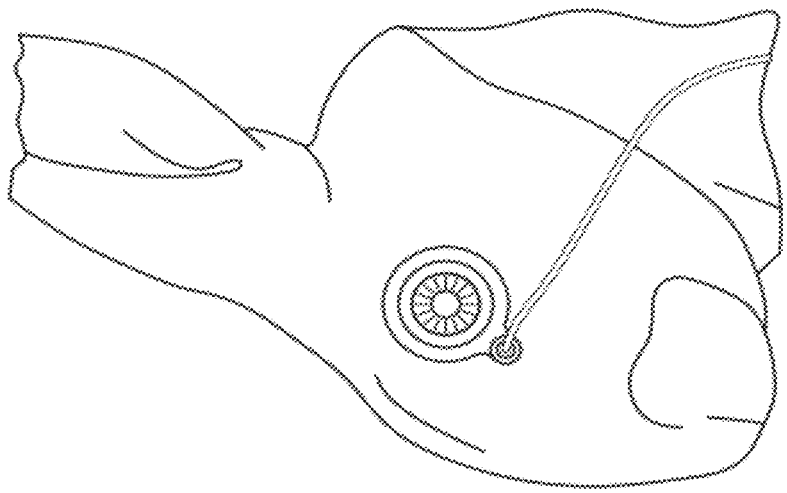
FIG. 5 is an image showing the setup of iontophoretic dosing in New Zealand rabbit eyes with the EyeGate II device and generator.
Figure 5:
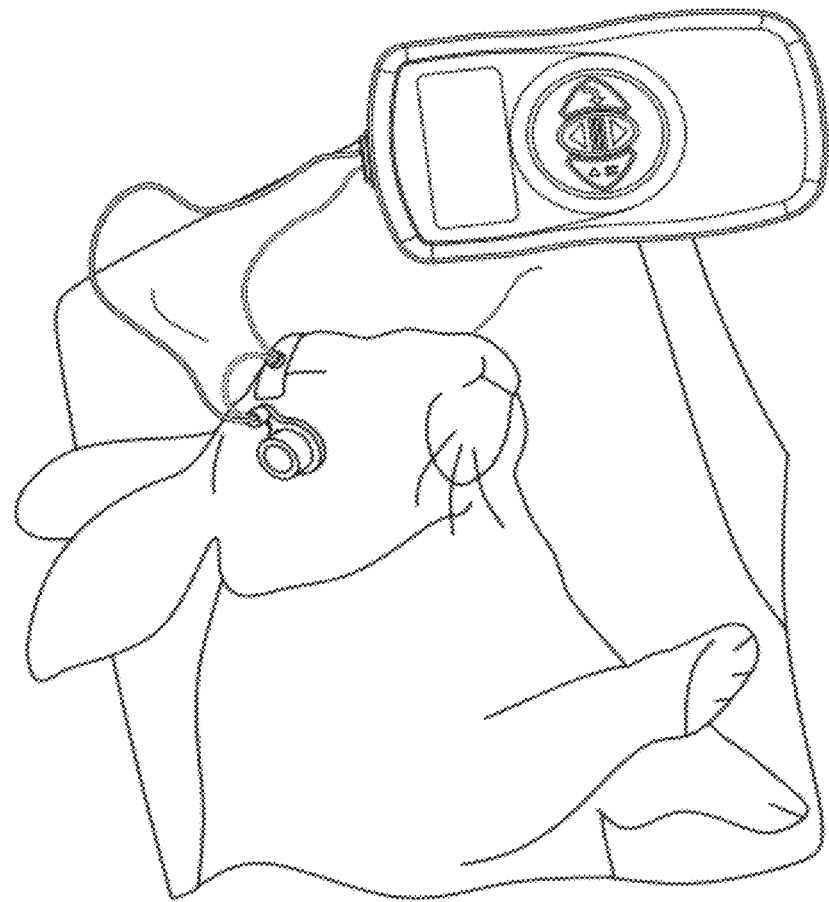
Figure 6:
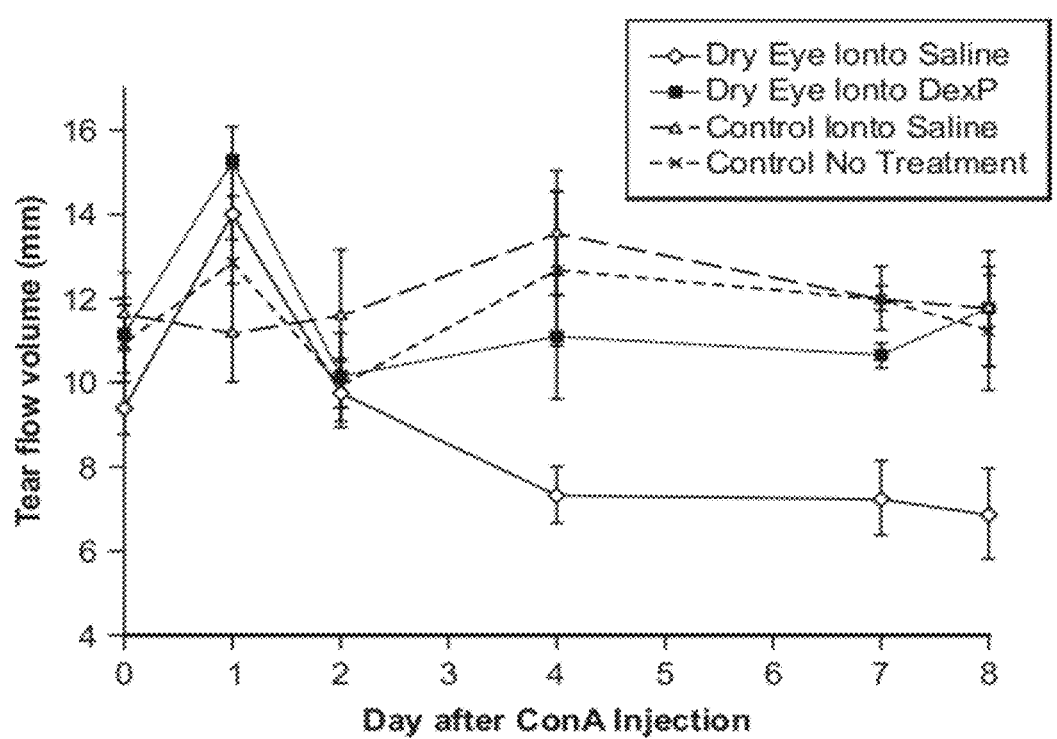
FIG. 6 is a graph showing tear flow measurement in rabbits injected in the lacrimal gland with either Concanavalin A or phosphate-buffered, saline (n=8 for each group). Rabbits were given a single iontophoretic dose of either dexamethasone phosphate or phosphate-buffered saline on Day 2. Tear flow was measured, with Schirmer strips and was recorded as the distance in mm of flow in 5 minutes. (*=P<0.01).
Figure 7:
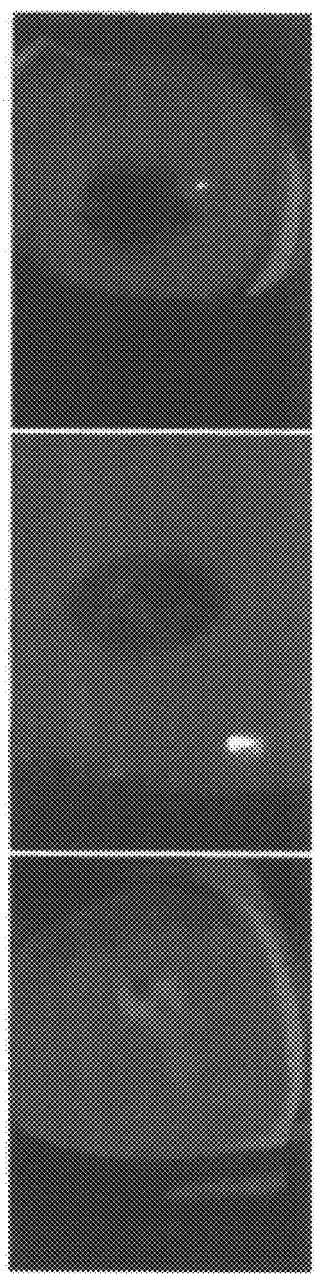
FIG. 7 are representative slit-lamp microscope images of fluorescein staining on the ocular surface of rabbits on Day 8 of the study. Left panel: Group 1—Rabbit had Con A-induced dry eye and was iontophoretically treated with saline on Day 2. Middle Panel: Group 2—Rabbit had Con A-induced dry eye and was iontophoretically treated with Dex-P on Day 2. Right panel: Group 3—Rabbit was injected with saline and was iontophoretically treated with saline on Day 2.
Figure 8:
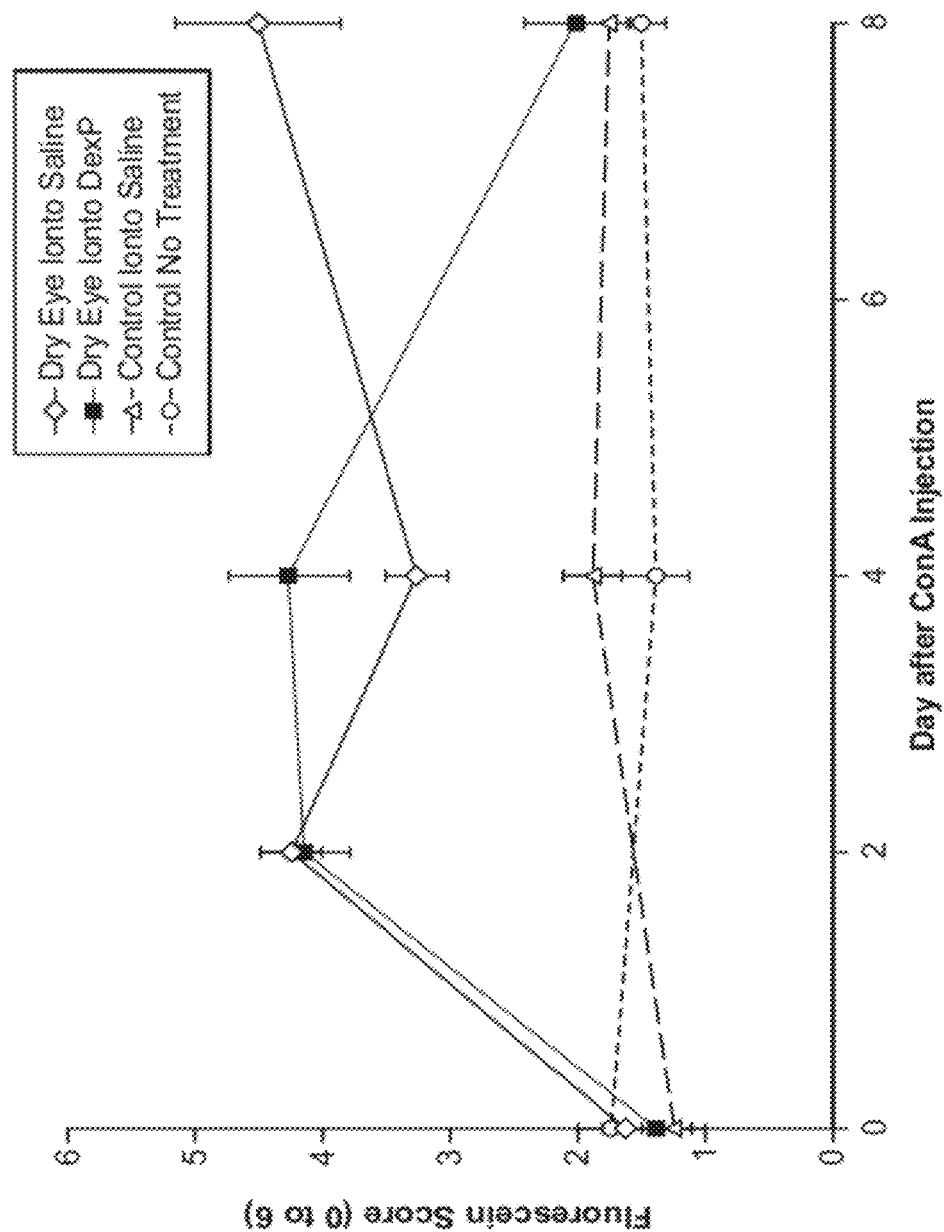
FIG. 8 is a graph showing fluorescein staining score in rabbits after a single iontophoretic dose of either dexamethasone phosphate solution or phosphate-buffered saline in the lacrimal gland (n=8 for each group). *=P<0.01).

Iontophoretic Drug Delivery 48 hours after lacrimal gland injection, rabbits were given a single 15 mA·min (−3.0 mA for 5 min) iontophoretic dose of dexamethasone phosphate (40 mg/mL) or phosphate-buffered saline using the EyeGate II device (EyeGate Pharmaceuticals, Inc) (FIG. 5). The animals were assigned to the following treatment groups:

Group 1: Con A injection on Day 0, Treatment with Dex-P on Day 2
Group 2: Con A injection on Day 0, Treatment with PBS on Day 2
Group 3: PBS injection on Day 0, Treatment with PBS on Day 2
Group 4: PBS injection on Day 0 with no subsequent treatment Clinical Observations Animals were observed daily following Con A injection for signs of ocular inflammation. Tear flow was measured using Schirmer strips in all groups on Days 0, 1, 2, 4, 7, and 8 after Con A injection (FIG. 6). Signs of ocular surface damage were assessed on Days 0, 2, 4, and 8 using fluorescein staining and slit-lamp microscopy (FIGS. 7 and 8). Staining was scored from 0 to 2 for superior, central, and inferior cornea for a total possible score of 6.

Cytokine Assays

Figure 9:
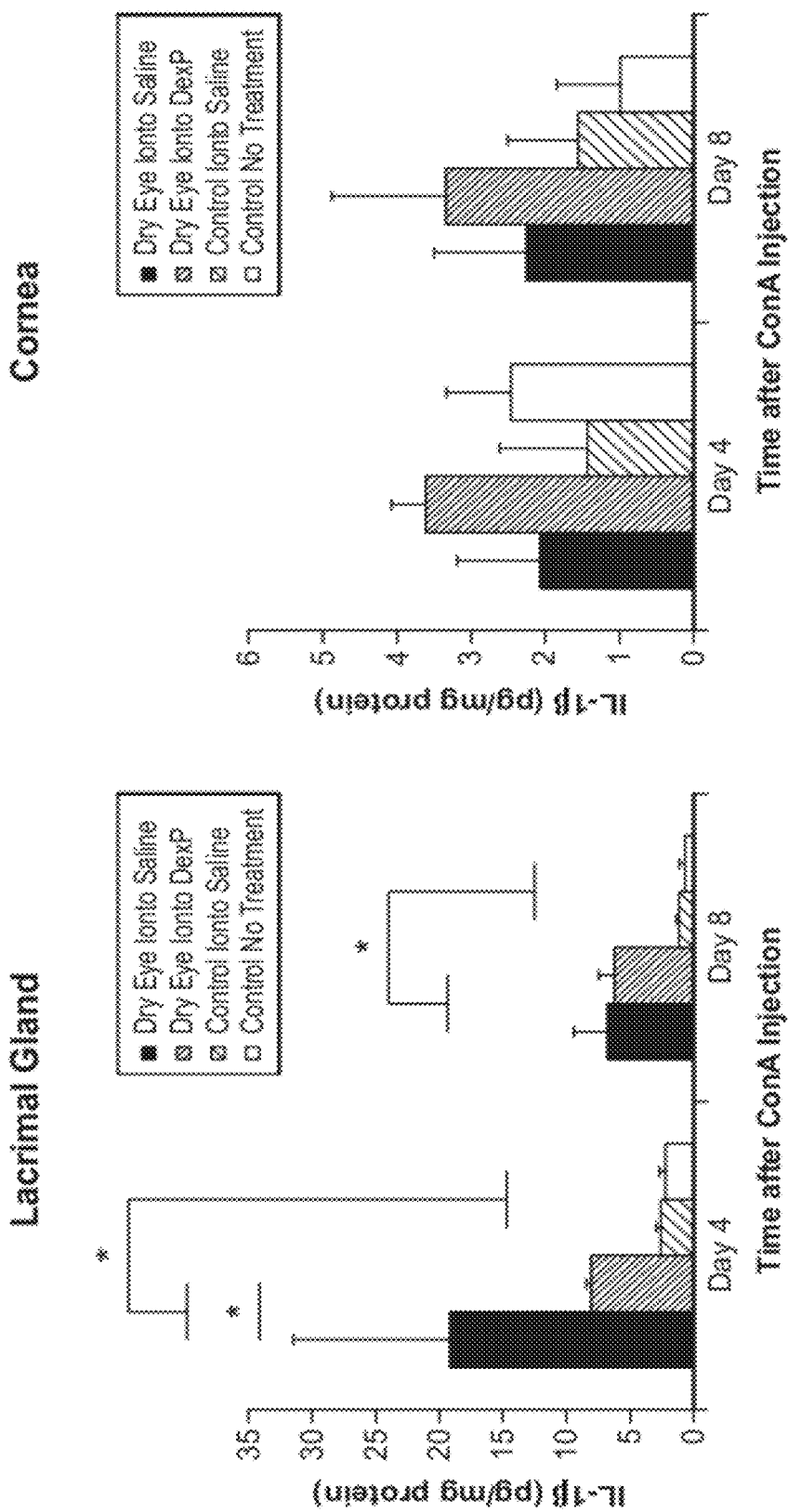
FIG. 9 is a graph showing the expression of interleukin-1beta (IL-1β) in the lacrimal glands and corneas of rabbits on Day 4 or Day 8 after lacrimal gland injection of concanavalin A or saline and iontophoretic treatment with dexamethasone phosphate or saline on Day 2. n=4, *=P<0.01. No significant difference was noted in the cornea, indicating a specific lacrimal gland inflammatory response.
Figure 10:
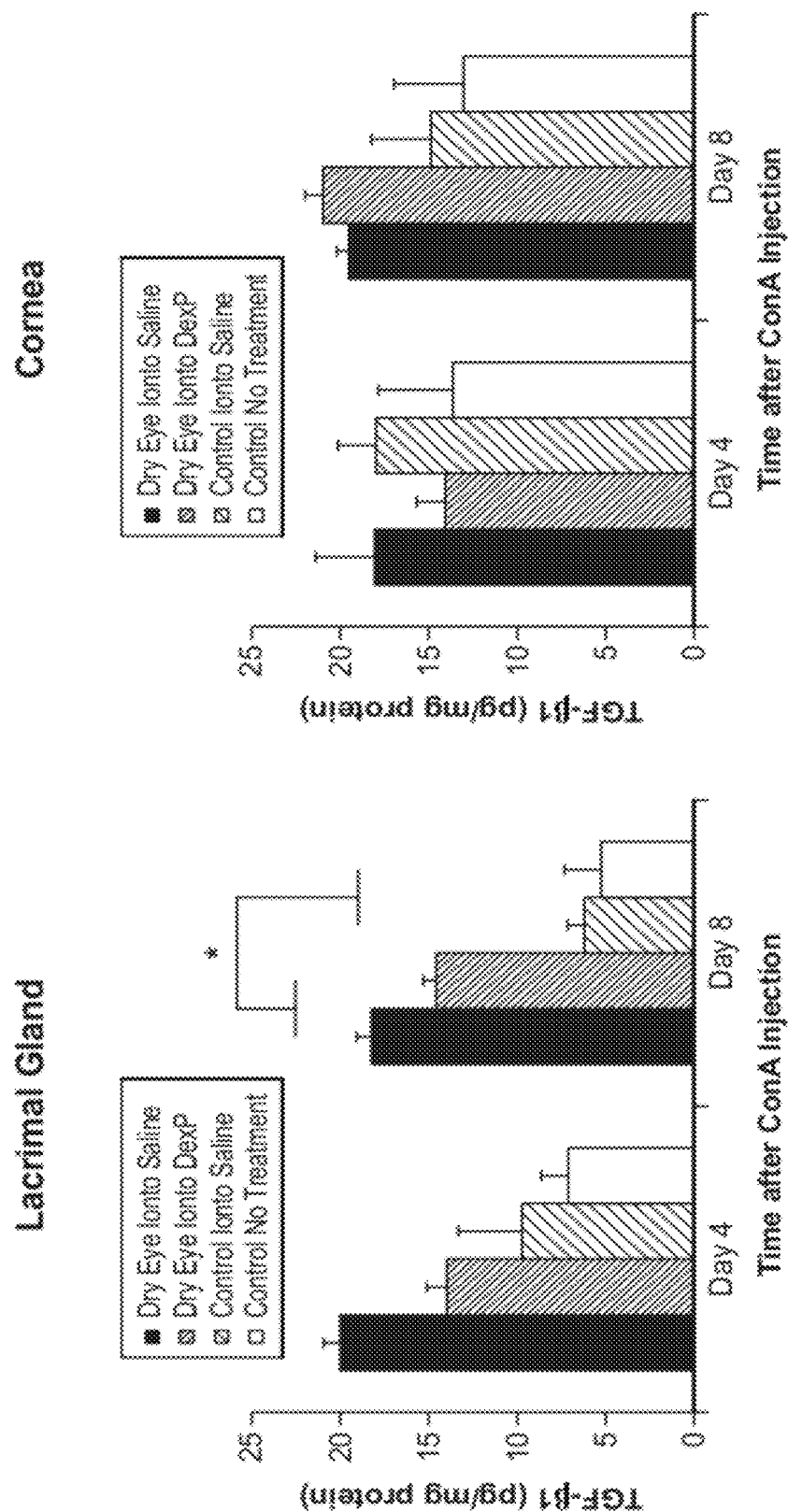
FIG. 10 is a graph showing expression of transforming growth factor beta-1 (TGF-β1) in the lacrimal glands and corneas of rabbits on Day 4 or Day 8 after lacrimal gland injection of concanavalin A or saline and iontophoretic treatment with dexamethasone phosphate or saline on Day 2. n=4, *=P<0.01. No significant difference was noted in the cornea, indicating a specific lacrimal gland inflammatory response.

Animals were euthanized on Day 4 or Day 8 following Con A injection. Upon sacrifice, the cornea and lacrimal gland were removed and snap frozen in liquid nitrogen followed by storage at −80° C. All samples were homogenized by hand in a ground-glass homogenizer in 0.5 mL of PBS+10 mM EDTA. Interleukin-1-beta (IL-1β), FIG. 9, and transforming growth factor beta-1 (TGF-β1), FIG. 10, were measured in lacrimal gland and corneal extracts using human IL-1β or TGF-β1 ELISA kit (R&D Systems DuoSet ELISA development system) according to manufacturer's instructions. Results were normalized for total protein concentration measured in the protein assay. Due to the high homology between rabbit and human IL-1β and TGF-β1, human kits are appropriate for detecting the rabbit cytokine.

Conclusions

A single iontophoretic dose of dexamethasone phosphate increases tear flow in rabbits and decreases the amount of ocular surface damage compared to control groups. Reduced IL-1β and TGF-β1 expression is observed in the lacrimal glands of eyes treated with a single iontophoretic dose of dexamethasone phosphate compared to saline treatment and control groups. No significant elevation of inflammatory cytokines in the cornea is observed on Day 4 and Day 8, indicating a specific inflammatory response of the lacrimal gland. A single iontophoretic dose of corticosteroid is a safer and more effective alternative than multiple, daily topical doses, Other Embodiments Other embodiments will be evident to those of skill in the art. It should be understood that the foregoing detailed description, is provided for clarity only and is merely exemplary. The spirit and scope of the present invention are not limited to the above examples, but are encompassed by the following claims. All references cited herein are incorporated by reference in their entireties.

What is claimed is:

1. An aqueous dexamethasone phosphate formulation comprising: (1) dexamethasone phosphate at a concentration of 40 mg/mL; and (ii) a buffering agent, wherein said buffering agent adjusts the pH of said formulation to 5.7 to 5.8.

* * * * *